United States Patent
Kulkarni et al.

(10) Patent No.: US 6,492,524 B1
(45) Date of Patent: Dec. 10, 2002

(54) PROCESS FOR THE SYNTHESIS OF AN ARYL PYRIDINE BASE USING A ZEOLITE CATALYST

(75) Inventors: Shivanand Janardan Kulkarni, Andhra Pradesh (IN); Kondapuram Vijaya Raghavan, Andhra Pradesh (IN); Srinivas Nagabandi, Andhra Pradesh (IN); Radha Rani Vippagunta, Andhra Pradesh (IN)

(73) Assignee: Council of Scientific and Industrial Research, New Delhi (IN)

(*) Notice: Subject to any disclaimer, the term of this patent is extended or adjusted under 35 U.S.C. 154(b) by 0 days.

(21) Appl. No.: 09/818,261

(22) Filed: Mar. 27, 2001

(51) Int. Cl.$^7$ ............... C07D 211/70; C07D 211/82
(52) U.S. Cl. ............ 546/348; 546/350; 546/352
(58) Field of Search ................ 546/348, 350, 546/352

(56) References Cited

U.S. PATENT DOCUMENTS

| | | | |
|---|---|---|---|
| 4,175,195 A | 11/1979 | Beschke et al. | 546/250 |
| 4,220,783 A | 9/1980 | Chang et al. | 546/251 |
| 4,675,410 A | * | 6/1987 | Feitler |
| 5,079,367 A | 1/1992 | Hoelderich et al. | 546/251 |
| 5,952,258 A | * | 9/1999 | Saitoh | |

FOREIGN PATENT DOCUMENTS

| | | |
|---|---|---|
| GB | 1233987 | 6/1971 |
| GB | 2020270 | 11/1979 |

OTHER PUBLICATIONS

Chemical Abstracts 93:46430, abstract of GB 2020270, 1979.*
Chemical Abstracts 89:163413, abstract of BE 858390, 1978.*
Cyhemical Abstract 128:75314, abstract of JP 09328470, 1997.*

* cited by examiner

Primary Examiner—D. Margaret Seaman
(74) Attorney, Agent, or Firm—Ladas & Parry

(57) ABSTRACT

The present invention provides an improved process for the synthesis of aryl pyridine bases by reacting an aromatic aldehyde or ketone and allylic alcohol or aldehyde in presence of ammonia in gas phase, in high yield and selectivity with catalyst obtained by optionally modifying a zeolite having an atomic ratio of Si to Al, 2.5 to 12.5 and /or with at least one metal ion and/or metal compound selected from the group consisting of lead and lanthanum. This process provides an eco-friendly, more economical and highly selective heterogeneous method.

23 Claims, No Drawings

PROCESS FOR THE SYNTHESIS OF AN ARYL PYRIDINE BASE USING A ZEOLITE CATALYST

FIELD OF THE INVENTION

The present invention relates to a process for the synthesis of an aryl pyridine base using a zeolite catalyst. More particularly, the present invention relates to a method for synthesizing phenyl pyridines directly from acetophenone and allyl alcohol in an eco-friendly, zeolite catalyzed heterogeneous method with high yields and selectivity. This invention provides a non-corrosive, eco-friendly process, where the life time of the catalyst is longer, it can be recycled and reused for many times, no-wastage of compounds (i.e. high atom selectivity) and high selectivity of the products.

BACKGROUND OF THE INVENTION

Phenyl pyridines have emerged as the integral backbone of several potent azapeptide HIV protease inhibitors with anti HIV activity such as BMS-232632a. Strategies for the synthesis of these phenyl pyridines by condensation and substitution reactions frequently afford low yields and cannot facilitate the synthesis of the 2-position selectively. A few homogeneous catalysts like Rh(1) have been reported for use in the selective alkylation of phenyl pyridine with olefins.

Zeolites of ZSM series are available from Conteka (Sweden). The methods for producing them are described in detail in U.S. Pat. Nos. 3,702,886 (ZSM-5), 3,709,979 (ZSM-11). HY is available from (PQ Corporation USA). HBEA is available from (Sud Chemie, India). HX is available from Aldrich. The synthesis of MCM-41 is disclosed in J. S. Beck et al, Nature 359 (1992) 710.

It is known that crystalline alumino silicate (zeolite) is used as a catalyst for producing pyridine bases from an aliphatic aldehyde and/or ketone and ammonia. ( U.S. Pat. No. 4,220,783 and Japanese patent application kokai (Laid-open) No. 38,362/85).

However, there are no reports available for the production of phenyl pyridines over a solid acid catalyst, except Japanese patent JP 01261367A/98 which discloses the synthesis of 2-phenyl-6-methyl pyridine over Si:Al catalyst starting with acetophenone, formaldehyde and acetone. The selectivity towards the phenyl pyridines in this patent is low. Another disadvantage of the process disclosed in JP 01261367A/98 is that it suffers from the selective synthesis of 2-phenyl pyridine without methyl group. Although a process for the synthesis phenyl pyridine using benzaldehyde and acetaldehyde is described in Ullmann's encyclopaedia A22, the major yield was only 4-phenyl pyridine.

Prior art processes suffer from the following disadvantages:
(a) in all the cases mineral acids are used as catalysts that are highly corrosive,
(b) non-reusability of the catalyst,
(c) in all the cases tedious work-up procedure is required, such as neutralization of acid etc.,
(d) in some cases more than a single step is require to synthesize phenyl pyridines selectively.

Increasing applications of these phenyl pyridines demands an eco-friendly, economical and free handling process. The present invention provides a eco-friendly process which can overcome all the above drawbacks.

OBJECTS OF THE INVENTION

The main object of the present invention is to provide a process for the synthesis of phenyl pyridine bases by using a specific zeolite catalyst, which is an eco-friendly heterogeneous catalytic method.

Another object of the present invention is to improve selectivity of the product.

SUMMARY OF THE INVENTION

Accordingly the present invention relates to a process for the synthesis of an aryl pyridine base said process comprising reacting an aromatic ketone of the formula $R_1COR_2$ wherein $R_1$ is phenyl or alkyl phenyl, $R_2$ is alkyl with 1 to 2 carbon atoms with the formula $R_3CH=CHCH_2$ OH wherein $R_3$ is selected from the group consisting of hydrogen, methyl, ethyl and aryl, with ammonia in a gaseous phase, the mole ratio of the aromatic ketone to allylic alcohol being in the range of 1:1 to 1:5, the mole ratio of ammonia to aromatic aldehyde and/or ketone being in the range of 0.5 to 5.0, the reaction temperature is in the range of 350° C. to 500° C., in the presence of a catalyst consisting of modified or unmodified zeolite having an atomic ratio of Si to Al in the range of 2.5 to 12.5 with at least one ion of and/or at least one compound of a metal selected from lead and lanthanum to obtain sais aryl pyridine base.

In one embodiment of the invention, the aryl ketone used is selected from acetophenone and methyl acetophenone.

In one embodiment of the invention, the aromatic aldehyde is phenyl acetaldehyde.

In one embodiment of the invention, the allylic alcohol is selected from allyl alcohol and crotyl alcohol.

In one embodiment of the invention, the aromatic ketone used comprises acetophenone and the allylic alcohol used comprises allyl alcohol to obtain 2-Phenyl pyridine.

In a further embodiment of the invention, the molar ratio of Acetophenone:allyl alcohol: ammonia is in the range of 1:1-3:0.5-5.

In one embodiment of the invention, the aromatic ketone used comprises acetophenone and is reacted with acrolein to obtain 2-phenyl pyridine.

In one embodiment of the invention, the aromatic aldehyde used comprises phenyl acetaldehyde and the allylic alcohol used comprises allyl alcohol to obtain 3-phenyl pyridine.

In one embodiment of the invention, the aromatic aldehyde used comprises phenyl acetaldehyde and is reacted with acrolein to obtain 3-phenyl pyridine.

In one embodiment of the invention, acetophenone is reacted with crotyl alcohol to yield 2-phenyl 4-methyl pyridine.

In one embodiment of the invention, acetophenone is reacted with crotonaldehyde to yield 2-phenyl 4-methyl pyridine.

In a further embodiment of the invention, methanol is added to the starting materials in an amount of up to 0.5 mole per mole of acetaldehyde.

In another embodiment of the invention, the zeolite used is in alkali ion form or ammonium ion form or proton form.

In a further embodiment of the invention, the alkali ion form of the zeolite is selected from sodium and potassium.

In a further embodiment of the invention, the zeolite catalyst is ion exchanged with a metal ion of a metal selected from the group consisting of lanthanum, thallium, lead and cobalt.

In yet another embodiment of the invention, the zeolite catalyst used is treated with at least one compound of a metal selected from the group consisting of lanthanum, lead and cobalt by impregnation, immersion, deposition or evaporation to dryness.

In yet another embodiment of the invention, the metal compound of lanthanum, lead and/or cobalt is at least one metal compound selected from the group consisting of oxides, halides, sulfates and phosphates.

In a further embodiment of the invention, the metal compound of lanthanum, lead and/or cobalt comprise oxides.

In yet another embodiment of the invention, the content of the metal compound of lanthanum, thallium, lead and/or cobalt is 0.1 to 5 wt % equivalent per g of the zeolite.

In yet another embodiment of the invention, crotyl alcohol is used as the allylic alcohol to obtain aryl picoline.

In another embodiment of the invention, the proportion of Si to Al in the zeolite is in the range of 2.5 to 140.

In yet another embodiment of the invention, the zeolite is selected from the group consisting of ZSM-5, ZSM-11, HY—a crystal structure of faujasite, HBEA Al-MCM-41, MCM-41 and HX.

In another embodiment of the invention, the catalyst comprises amorphous silica-alumina.

The present invention also relates to develop a process for the preparation of phenyl pyridines of the formula

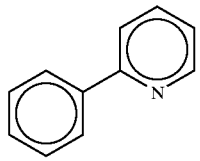

from acetophenone and allyl alcohol over a zeolite catalyst.

DETAILED DESCRIPTION OF THE INVENTION

Aryl pyridine bases are obtained according to the process of this invention by reacting an aryl aldehyde and/or ketone with allylic alcohols (alkenyl alcohol or aldehyde) in presence of ammonia in gaseous phase in the presence of a catalyst, which is selected from varied Si :Al ratio in the range 2.5 to 140 or a catalyst with a particular Si/Al ratio modified with at least one metal compound selected from the group consisting of lanthanum compounds, lead compounds and cobalt compounds by impregnation or ion exchange methods. Among zeolites, those having an atomic ratio of Si to Al 2.5 to 140 can be used as the starting materials for preparing the catalysts to be used in the present invention, which show a high catalytic performance.

The zeolites which can be used as the starting materials for preparing the catalysts to be used in the present invention are exemplified as several zeolites including aluminosilicate such as ZSM-type, HY, Al-MCM-41, H-BEA, HX. From these except MCM-41 other zeolites are easily commercially available, and also are prepared by methods known in the literature. For example, zeolites of ZSM series are available from Conteka (Sweden). The methods for producing them are described in detail in U.S. Pat. Nos. 3,702,886 (ZSM-5), 3,709,979 (ZSM-11), HY is obtained from (PQ corporation USA), HBEA was obtained from (Sud chemie, India), HX was from Aldrich and MCM-41 was synthesized by known art according to (J. S. Beck et. al., Nature 359 (1992) 710).

Furthermore, the zeolite used in the present invention may be in any of the alkali ion form such as sodium, potassium or ammonium ion form and proton form. The alkali ion, however, is not preferably because it lowers the catalytic activity, and hence it is desirable to eliminate the alkali ion before, during or after modifying the zeolite with ion of and/or compound of metal selected from the group consisting of lanthanum, lead and/or cobalt. The zeolite to be subjected to impregnation is treatment with lanthanum, lead and/or cobalt ions may be in any one of alkali ion form, ammonium ion form or proton form, and the most preferable is ammonium form zeolite. Accordingly, it is desirable that a zeolite of an alkali ion form or proton form is previously ion exchanged into ammonium form by dipping it repeatedly for several times in an aqueous solution of an ammonium salt such as ammonium chloride, ammonium nitrate, ammonium acetate or in aqueous ammonia and then filtering it.

A zeolite alkali ion form, ammonium form or proton form, preferably of proton form is added to an aqueous solution of at least one metal compound selected from the group consisting of lanthanum compounds, lead compounds and cobalt compounds with a concentration of 0.5 to 10 wt % per gram catalyst and soaked for several hours finally evaporated the water. After the procedure, the modified zeolite is usually dried at 100° C. to 200° C. and if desired, calcined at 350 to 450° C. to obtain a catalyst.

Though the calcination is conducted usually in air or in a gas such as nitrogen or the like at 350° C. to 500° C. for several hours, the calcination is not always necessary because the catalyst is heated in a reactor.

The content of lanthanum, lead and/or cobalt in the zeolite which has been modified with the corresponding metallic ions and/or compounds is about 0.5 to 10 wt % equivalent/g, though the preferable region varies depending on the kind of the zeolite and of the metal ion and compound.

The zeolite which has been ion exchanged with lanthanum ion, lead ion and/or cobalt ion or the zeolite which has been treated with at least one metal compound selected from thallium compounds, lead compounds and/or cobalt compounds by a method of impregnation, deposition or evaporation to dryness is molded as it is or after pelletization to a tablet and made it to 18–30 mesh.

In either method, the molded product is calcined in the atmosphere or in a gas such as nitrogen or the like at 350° C. to 600° C. for several hours to impart strength to the molded product and to eliminate volatile components which had been contained in the binder. However, because the catalyst is heated in a reactor, the calcination is not always necessary.

The aryl ketone used in the present invention includes acetophenone, methyl acetophenone and alkenyl alcohol or aldehydes and allyl alcohol, crotyl alcohol, acrolein or crotonaldehyde.

The combination of aromatic aldehydes and/or ketones as the starting materials with alkenyl alcohol determines the main phenyl pyridine bases produced. Typical examples are shown in the Table 1.

TABLE 1

| Reactant 1 | Reactant 2 | Main products formed |
|---|---|---|
| Acetophenone | allyl alcohol | 2-phenyl pyridine |
| Acetophenone | acrolein | 2-phenyl pyridine |
| Phenyl acetaldehyde | allyl alcohol | 3-phenyl pyridine |
| Phenyl acetaldehyde | acrolein | 3-phenyl pyridine |

TABLE 1-continued

| Reactant 1 | Reactant 2 | Main products formed |
|---|---|---|
| Acetophenone | crotyl alcohol | 2-phenyl 4-methyl pyridine |
| Acetophenone | crotanaldehyde | 2-phenyl 4-methyl pyridine |

The reaction of the present invention is conducted in a mode of fixed bed.

The molar ratio of ammonia to the aromatic aldehyde and/or ketone is 0.5 to 5 mol/mol. The weitht hourly space velocity (WHSV) used is 0.25 to 1.00. The reaction temperature is preferably 300° C. to 400° C. Although the pressure of the reaction gases can be used in the range of from below the atmospheric pressure to several atmospheric pressures, usually the pressure in the range of from the atmospheric pressure to about 2 atmospheric pressures is used conveniently.

In particular, preferable combination of an aromatic aldehyde or ketone with alkenyl alcohol or aldehyde for the production of phenyl pyridine or phenyl picolines the molar ratio of acetophenone: allylalcohol: ammonia is adjusted to 1:1-3: 0.5-5.

In particular, in this reaction one other side product observed is 3-picoline which is also an important drug intermediate.

Although deposition of carbon on the catalyst is detected during the reaction, the amount of the carbon deposited on the catalyst is smaller as a result of which higher yield of 2-phenyl pyridine is obtained.

The regeneration of the catalyst is easily effected by any conventional method such as burning out the carbon deposited on the catalyst by passing air through the catalyst layer at a temperature of 450° C. to 550° C. The products were trapped by cooling at the bottom and analyzed by GC, confirmed by NMR and GC-MS.

By using the catalyst of the present invention, as shown, for example, in Example 1, the yield of 2 phenyl pyridine is 63% and 81%, respectively, the yields being shown as the value calculated based on the conversion of acetophenone.

2-phenyl pyridine can be obtained in a higher yield as compared with in conventional processes. Also, the amount of carbon deposited on the catalyst is small and the regeneration of the catalyst is easy.

The present invention is described below in more detail referring to Examples, to which the present invention is not limited. The results in examples are calculated based on the conversion of acetophenone.

EXAMPLE 1

According to method [J. S. Beck et. al., Nature 359 (1992) 710], mesoporous molecular sieve Al-MCM41zeolite ZSM-5 was synthesized as follows.

Solution A was prepared by mixing 0.38 g of NaOH, 20 ml of water, 0.76 g of Aluminum isopropoxide and heated till a clear solution was obtained. After this 9.8 ml of Tetra ethyl ammonium hydroxide was added while cooling the mixture. Solution B was prepared by mixing 11.6 ml (9.6 g) of 50 wt % ludox silica in 50 ml of distilled water the mixture was kept under vigorous stirring until a clear solution formed.

Solution A was added to Solution B under vigorous stirring and kept for stirring for one hour, after that 10.55 g of Hexadecyl trimethyl ammonium bromide (HDTMABr). The pH was adjusted to 10.5. A stainless steel autoclave having 0.6 liters of volume was charged with the above solution. The autoclave was sealed and heated to 100° C. Hydro thermal synthesis was effected under this condition while continuing stirring for 20 hours. In this period, the inner pressure of the autoclave was 5 to 6 kg/cm. sup.2.

After completion of the reaction, the reaction mixture was cooled to room temperature and the product was separated by filtration. After repetition of washing and filtration until the concentration of Br$^-$ ion in the filtrate became 1 ppm or below, the product was dried at 110° C. for 16 hours and then calcined in air at 500° C. for 12 hours to elute the surfactant. White crystals of Na form Al-MCM-41 were obtained. As a result of the measurement of X-ray diffraction, the crystals had a diffraction pattern coincident with that of MCM-41 reported in Nature 1992 by Breck et al. The catalyst was then pelletized and made to 18–30 size mesh.

EXAMPLE 2

A glass reaction tube having an inner diameter of 20 mm was filled with 4 g of this crystalline Al-MCM-41 catalyst. A mixture of 1 moles of acetophenone two mole of allyl alcohol fed on to the packed catalyst through preheating zone in gas form along with ammonia and the temperature maintained 360° C. at the catalyst bed. The reaction products were collected at bottom through ice cold traps and analyzed by a FID gas chromatography.

Average yields of the products in a period of 4 hours from the start of the reaction were found 90% of 2-Phenyl pyridine, 10.0% of pyridine and other products. An other major product is 3-picoline which forms by the cyclization of only allyl alcohol in presence of ammonia.

EXAMPLE 3

The reaction carried out in same manner as in example 2 with HY catalyst, the selectivity of 2-Phenyl pyridine is 84.9% at the conversion of acetophenone is 98.0 wt %.

EXAMPLE 4

The reaction carried out in same manner as in example 2 with HZSM-5 (30) catalyst, the selectivity of 2-Phenyl pyridine is 57.5% at the conversion of acetophenone is 65.0 wt %.

EXAMPLE 5

The reaction carried out in same manner as in example 2 with H-BEA catalyst, the selectivity of 2-Phenyl pyridine is 26.5% at the conversion of acetophenone is 65.2 wt %.

EXAMPLE 6

The reaction carried out in same manner as in example 2 with HX catalyst, the selectivity of 2-Phenyl pyridine is 67.6% at the conversion of acetophenone is 27.5 wt %.

EXAMPLE 7

The reaction carried out in same manner as in example 2 with Silica-Alumina catalyst, the selectivity of 2-Phenyl pyridine is 41.6% at the conversion of acetophenone is 42.0 wt %.

EXAMPLE 8

Proton form of Y catalyst was soaked in the 5 wt % aqueous of solution lead (lead nitrite is source of lead) for several hours then the solution was evaporated and catalyst was dried by calcination at 420° C. for four hours.

The reaction was carried out in same manner of Example 2, the selectivity of 2-phenyl pyridine is 86.3% at the conversion of acetophenone is 100 wt %.

EXAMPLE 9

LaY (metal content: 5 wt %) having a Si/Al atomic ratio of 5 was prepared by a method similar to that described in Example 8, the selectivity of 2-phenyl pyridine is 92.2% at the conversion of acetophenone is 100 wt %.

EXAMPLE 10

The result of the same reaction as in Example 8 except the reaction temperature is varied is shown in Table 1

TABLE 1

| | | | | Yield of products | |
| --- | --- | --- | --- | --- | --- |
| S. No. | Temperature (° C.) | TOS (h) | Conversion of Acetophenone (%) | 2-phenyl pyridine | Methyl phenyl pyridine |
| 1 | 400 | 4 | 72.5 | 54.8 | 4.0 |
| 2 | 360 | 4 | 76.8 | 69.4 | 8.0 |
| 3 | 300 | 4 | 95.2 | 71.0 | — |
| 4 | 250 | 4 | 8.4 | 5.0 | — |

Feed: allyl alcohol+acetophenone+NH$_3$, Catalyst: PbY; whsv: 0.5 h$^-$

EXAMPLE 11

The reaction was carried in same manner as in Example 2 except crotyl alcohol was used instead of allyl alohol and the final product was 2-phenyl 4 methyl pyridine.

EXAMPLE 12

The reaction was carried in same manner as in Example 2 except phenyl acetaldehyde was used instead of acetophenone and the final product was 3-phenyl pyridine.

EXAMPLE 13

The reaction was carried in same manner as in Example 2 except methyl acetophenone instead of acetophenone and the final product was 2-(methyl phenyl) pyridine.

Phenyl pyridines are integral backbone of several potent azapeptide HIV protease inhibitors with an anti HIV activity such as BMS-232632a.

Advantages of the Invention

The present invention provides a process that comprises of environmentally clean and economical technology, easily recycled and reusability of the catalyst

- The process provides an eco-friendly method with high selectivity towards the product.
- This method provides a selective heterogeneous catalyst with longer life.
- Further, this method provides a route, wherein the kind and composition of phenyl pyridines can be varied by varying the substituents on the reactants.
- It also provides an efficient and economical method for synthesizing phenyl pyridines from acetophenone and allyl alcohol over zeolite catalyst in gas phase.

We claim:

1. A process for the synthesis of an aryl pyridine base said process comprising reacting an aromatic aldehyde or ketone of the formula R$_1$COR$_2$ wherein R$_1$ is phenyl or alkyl phenyl, R$_2$ is alkyl with 1 to 2 carbon atoms with an acrolein or crotonaldehyde or an allylic alcohol of the formula R$_3$CH=CHCH$_2$OH wherein R$_3$ is selected from the group consisting of hydrogen, methyl, ethyl and aryl, with ammonia in a gaseous phase, the mole ratio of the aromatic aldehyde or ketone to allylic alcohol being in the range of 1:1 to 1:5, the mole ratio of ammonia to aromatic aldehyde and/or ketone being in the range of 0.5 to 5.0, at a reaction temperature in the range of 350° C. to 500° C., in the presence of a catalyst consisting of modified or unmodified zeolite having an atomic ratio of Si to Al in the range of 2.5 to 12.5 with at least one ion of and/or at least one compound of a metal selected from lead and lanthanum, to obtain said aryl pyridine base.

2. A process as claimed in claim 1 wherein the aryl ketone used is selected from acetophenone and methyl acetophenone.

3. A process as claimed in claim 1 wherein the aromatic aldehyde is phenyl acetaldehyde.

4. A process as claimed in claim 1 wherein the allylic alcohol is selected from allyl alcohol and crotyl alcohol.

5. A process as claimed in claim 1 wherein the aromatic ketone used comprises acetophenone and the allylic alcohol used comprises allyl alcohol to obtain 2-Phenyl pyridine.

6. A process as claimed in claim 5 wherein the molar ratio of Acetophenone:allyl alcohol: ammonia is in the range of 1: 1-3:0.5-5.

7. A process as claimed in claim 1 wherein the aromatic ketone used comprises acetophenone and is reacted with acrolein to obtain 2-phenyl pyridine.

8. A process as claimed in claim 1 wherein the aromatic aldehyde used comprises phenyl acetaldehyde and the allylic alcohol used comprises allyl alcohol to obtain 3-phenyl pyridine.

9. A process as claimed in claim 1 wherein the aromatic aldehyde used comprises phenyl acetaldehyde and is reacted with acrolein to obtain 3-phenyl pyridine.

10. A process as claimed in claim 1 wherein acetophenone is reacted with crotyl alcohol to yield 2-phenyl 4-methyl pyridine.

11. A process as claimed in claim 1 wherein acetophenone is reacted with crotonaldehyde to yield 2-phenyl 4-methyl pyridine.

12. A process as claimed in claim 1 wherein methanol is added to the starting materials in an amount of up to 0.5 mole per mole of acetaldehyde.

13. A process as claimed in claim 1 wherein the zeolite used is in alkali ion form or ammonium ion form or proton form.

14. A process as claimed in claim 13 wherein the alkali ion form of the zeolite is selected from sodium and potassium.

15. A process as claimed in claim 1 wherein the zeolite catalyst is ion exchanged with a metal ion of a metal selected from the group consisting of lanthanum, thallium, lead and cobalt.

16. A process as claimed in claim 15 wherein the zeolite catalyst used is treated with at least one compound of a metal selected from the group consisting of lanthanum, lead and cobalt by impregnation, immersion, deposition or evaporation to dryness.

17. A process as claimed in claim 15 wherein the metal compound of lanthanum, lead and/or cobalt is at least one metal compound selected from the group consisting of oxides, halides, sulfates and phosphates.

18. A process as claimed in claim 17 wherein the metal compound of lanthanum, lead and/or cobalt comprise oxides.

19. A process as claimed in claim 15 wherein the content of the metal compound of lanthanum, thallium, lead and/or cobalt is 0.1 to 5 wt % equivalent per g of the zeolite.

20. A process as claimed in claim 1 wherein the allylic alcohol used comprises crotyl alcohol to obtain aryl picoline.

21. A process as claimed in claim 1 wherein the proportion of Si to Al in the zeolite is in the range of 2.5 to 140.

22. A process as claimed in claim 1 wherein the zeolite is selected from the group consisting of ZSM-5, ZSM-1 1, HY—a crystal structure of faujasite, HBEA Al-MCM-4 1, MCM-41 and HX.

23. A process as claimed in claim 1 wherein the catalyst comprises amorphous silica-alumina.

* * * * *